(12) United States Patent
Hochrainer et al.

(10) Patent No.: US 6,986,346 B2
(45) Date of Patent: *Jan. 17, 2006

(54) CLOSURE-CAP AND CONTAINER AS A TWO-CHAMBER CARTRIDGE FOR NEBULISERS FOR PRODUCING AEROSOLS AND ACTIVE SUBSTANCE FORMULATIONS, SUITABLE FOR STORAGE

(75) Inventors: Dieter Hochrainer, Bingen (DE); Bernd Zierenberg, Bingen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 76 days.

This patent is subject to a terminal disclaimer.

(21) Appl. No.: 10/256,781

(22) Filed: Sep. 27, 2002

(65) Prior Publication Data

US 2003/0066524 A1 Apr. 10, 2003

Related U.S. Application Data

(63) Continuation of application No. 09/871,500, filed on May 31, 2001, now Pat. No. 6,481,435, which is a continuation of application No. 09/416,476, filed on Oct. 12, 1999, now abandoned.

(60) Provisional application No. 60/112,380, filed on Dec. 14, 1998.

(30) Foreign Application Priority Data

Oct. 17, 1998 (DE) .......................................... 198 47 970
Oct. 17, 1998 (DE) .......................................... 198 47 968

(51) Int. Cl.
    A61M 11/00  (2006.01)
    A61M 37/00  (2006.01)
    B65D 35/22  (2006.01)

(52) U.S. Cl. ...................... 128/200.19; 604/86; 604/87; 604/89; 206/219; 366/130; 222/94

(58) Field of Classification Search ............ 128/200.14, 128/210.14; 604/85, 86, 87–89, 90–92, 410–412, 604/414–416, 903, 905; 366/130, 347; 206/219, 206/222, 538, 221; 222/80, 81, 83, 92–94; 215/227, 250–251, 270, DIG. 8, DIG. 3; 220/258.1–258.4, 200

See application file for complete search history.

(56) References Cited

U.S. PATENT DOCUMENTS

| | | | |
|---|---|---|---|
| 2,362,103 A | | 11/1944 | Smith |
| 2,793,776 A | * | 5/1957 | Lipari ......................... 206/221 |
| 3,172,568 A | * | 3/1965 | Modderno .................... 222/80 |
| 3,354,883 A | * | 11/1967 | Southerland ................. 604/88 |
| 3,655,096 A | * | 4/1972 | Easter .......................... 222/82 |
| 3,842,836 A | | 10/1974 | Ogle |
| 3,858,580 A | * | 1/1975 | Ogle ............................ 604/91 |
| 3,870,147 A | * | 3/1975 | Orth ............................ 206/222 |
| 3,924,741 A | * | 12/1975 | Kachur et al. ............... 206/221 |
| 3,946,732 A | * | 3/1976 | Hurscham .................... 604/88 |
| 3,949,751 A | * | 4/1976 | Birch et al. ............ 128/203.15 |

(Continued)

FOREIGN PATENT DOCUMENTS

| CA | 2251828 | 10/1997 |
|---|---|---|
| DE | 196 15 422 A1 | 11/1997 |

*Primary Examiner*—Mital Patel
(74) *Attorney, Agent, or Firm*—Thomas C. Blankinship; Timothy X. Witkowski; Mary-Ellen Devlin

(57) ABSTRACT

The invention relates to an apparatus comprising a closure-cap and a container in the form of a two-chamber cartridge in which an active ingredient and a solvent can be stored separately until the apparatus is used in a nebuliser, as well as an active substance concentrate in which the active substance is present as a solution or suspension for storage purposes.

52 Claims, 7 Drawing Sheets

U.S. PATENT DOCUMENTS

| | | | | |
|---|---|---|---|---|
| 4,174,035 A | * | 11/1979 | Wiegner | 206/222 |
| 4,177,938 A | * | 12/1979 | Brina | 222/80 |
| 4,195,730 A | * | 4/1980 | Hunt | 206/221 |
| 4,315,570 A | * | 2/1982 | Silver et al. | 206/221 |
| 4,515,586 A | * | 5/1985 | Mendenhall et al. | 604/87 |
| 4,516,967 A | * | 5/1985 | Kopfer | 604/87 |
| 4,727,985 A | | 3/1988 | McNeirney et al. | |
| 4,821,923 A | * | 4/1989 | Skorka | 222/80 |
| 4,979,941 A | * | 12/1990 | Ogle, II | 604/82 |
| 4,982,875 A | * | 1/1991 | Pozzi et al. | 222/83 |
| 5,246,142 A | * | 9/1993 | DiPalma et al. | 222/129 |
| 5,533,994 A | | 7/1996 | Meyer | |
| 5,569,191 A | * | 10/1996 | Meyer | 604/82 |
| 5,685,846 A | * | 11/1997 | Michaels, Jr. | 604/90 |
| 5,782,345 A | | 7/1998 | Guasch et al. | |
| 5,827,262 A | * | 10/1998 | Neftel et al. | 604/414 |
| 5,935,101 A | * | 8/1999 | Kato et al. | 604/82 |
| 6,041,969 A | * | 3/2000 | Parise | 222/129 |
| 6,152,296 A | * | 11/2000 | Shih | 206/222 |
| 6,481,435 B2 | * | 11/2002 | Hochrainer et al. | 128/200.14 |

* cited by examiner

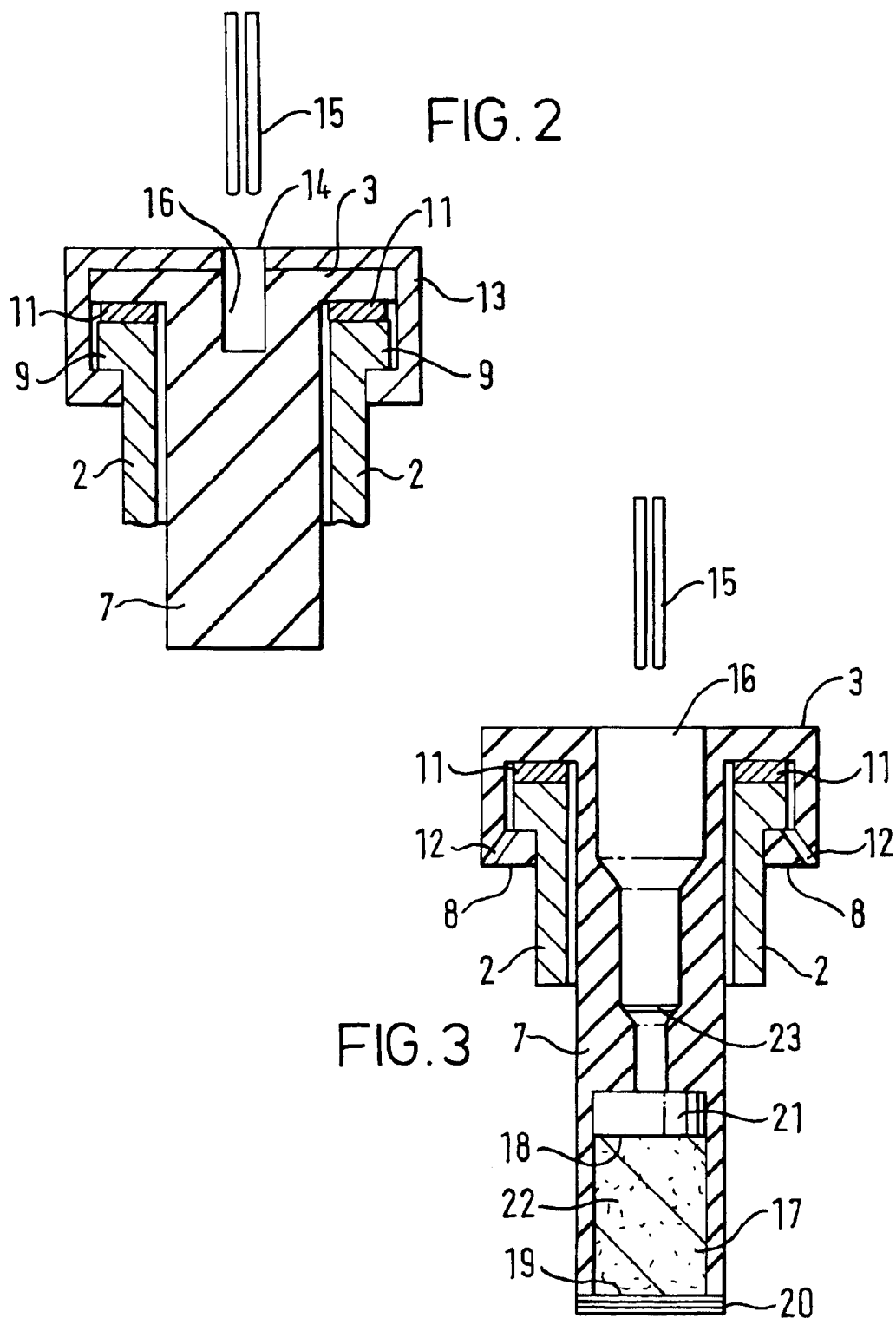

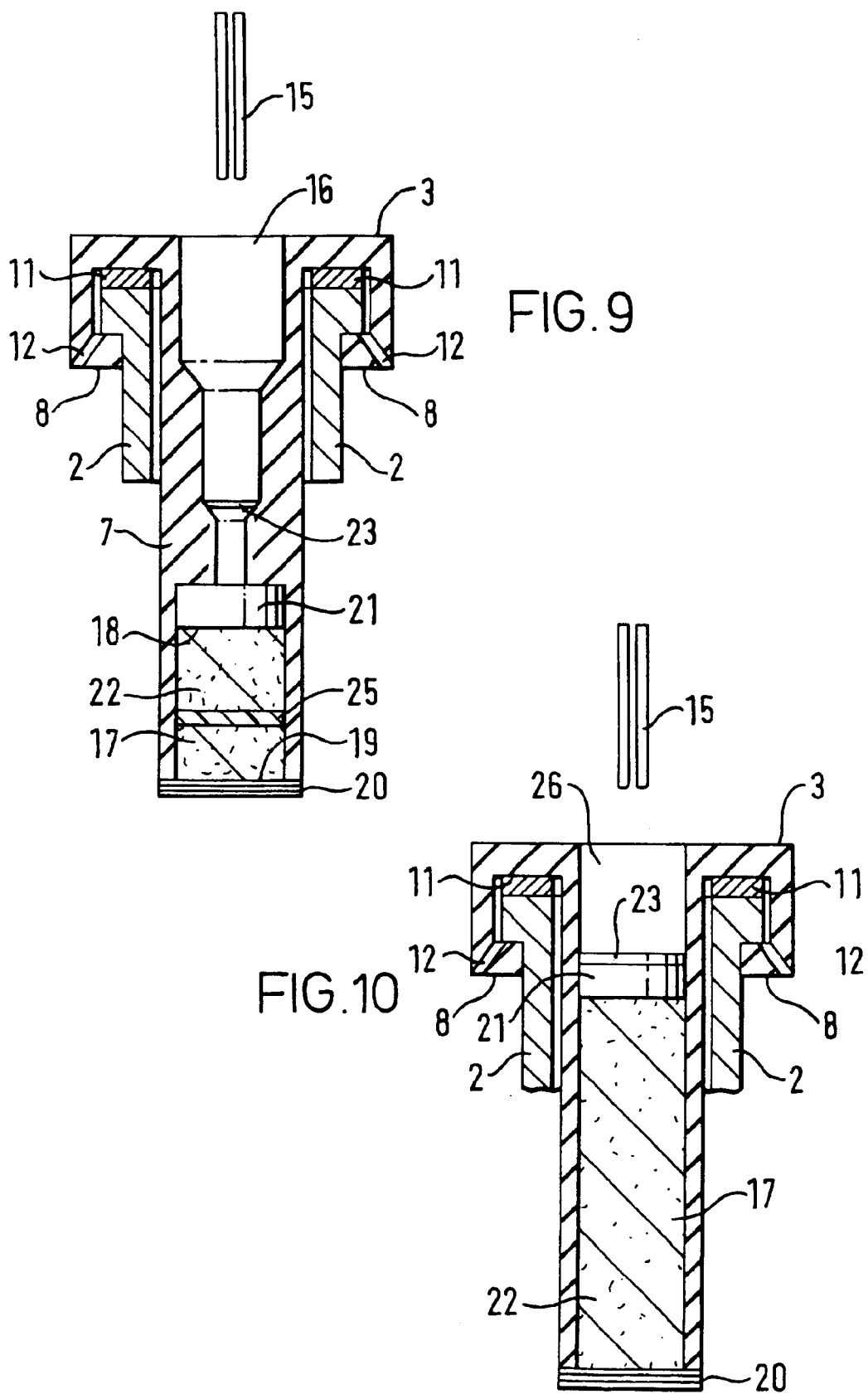

CLOSURE-CAP AND CONTAINER AS A TWO-CHAMBER CARTRIDGE FOR NEBULISERS FOR PRODUCING AEROSOLS AND ACTIVE SUBSTANCE FORMULATIONS, SUITABLE FOR STORAGE

The present invention relates to an apparatus comprising a closure-cap and a container in the form of a two-chamber cartridge in which an active ingredient and a solvent can be stored separately until the apparatus is used in a nebuliser, and to a propellant-free active substance concentrate in which the active ingredient is present in highly-concentrated form for storage purposes. The cartridge according to the invention serves especially as a container for medicament formulations for use in nebulisers for production of aerosols for inhalative or nasal application, especially for use in propellant-free nebulisers.

In the International Patent Application WO91/14468 "Atomising Device and Methods" and also in WO 97/12687, cf FIGS. 6a and 6B and the associated description, an apparatus for the propellant-free administration of a metered quantity of a fluid medicament for inhalative application is described. In such a nebuliser, a medicament solution is converted by means of high pressure into a lung-accessible aerosol and sprayed. For this kind of application, it can be necessary to decant the solutions which contain the active ingredients into containers so that only a small amount of air and gas residue is included. Containers which are suitable for this purpose, are, for example, disclosed in International Patent Application PCT/EP95/03183, to which express reference will be made for the purposes of the present invention. The containers described there are above all suitable for those medicaments which can be stored over a longer period of time in the form of an aqueous or ethanolic solution.

In order to increase the shelf-life of active ingredients in solution which break down after only a few months, DE 196 15 422 discloses a cartridge which has two chambers for the separate storage of the solvent and an active ingredient in the form of a powder or a compressed tablet. The cartridge is designed in such a way that when the cartridge is inserted in apparatus for the production of the aerosol (inhaler), the chamber which contains the active ingredient is penetrated by a canula in the inhaler, so that the active ingredient comes into contact with the solvent in the container and is dissolved. Although this cartridge for storing inhalation formulations in the aforementioned containers has many advantages, from time to time the canula of the inhaler, as specified, can become blocked when it penetrates the chamber which contains the active ingredient. For this reason, no medicament suspensions can be stored in the aforementioned chamber. Furthermore, it can not always be guaranteed that active ingredients formulated as a solid will dissolve sufficiently rapidly in the solvent, so that the desired active ingredient concentration can only be achieved with a time delay. In this way, trouble-free use of the inhaler charged with the cartridge is made difficult.

The present invention solves the aforementioned problems and also those known from the prior art in that a new two or multi-chamber cartridge (container) is provided where two or more components of the inhalation formulation can be stored separately from one another.

In particular, the invention relates to an apparatus comprising a closure-cap and a container which can be used as a cartridge (container) for nebulisers. In the cartridge, at least one active ingredient and one solvent of a therapeutic formulation specified for inhalative or nasal application can be stored separately until the cartridge is installed in the nebuliser as specified. As nebulisers, high-pressure atomisers and especially the high-pressure atomisers from WO91/14468 and WO 97/12687, FIGS. 6a and 6b and the associated description, are particularly suitable. Here, the cartridge is shaped so that the separately-stored components can be mixed together during use of the cartridge in the inhaler without causing a blockage of the canula, so that the medicament preparation is formed, ready for use, within the shortest possible time, preferably within a few minutes and possibly within a few seconds. In the context of the present invention, it is unimportant whether the medicament formulation which is to be applied is a solution or a suspension; what is critical is that the formulation which is to be applied is a fluid formulation which can be converted by means of a nebuliser of the aforementioned type into an aerosol for inhalative or nasal application. For administration by inhaling using the inhaler described hereinbefore, however, formulations in the form of solutions are generally preferred to those in the form of suspensions.

Within the scope of this description, the expressions nebuliser, atomiser, inhaler and high-pressure atomiser, and also metering aerosol and aerosol are used as synonyms unless otherwise stated.

DESCRIPTION OF THE INVENTION

The present invention is constructed in a similar manner to the invention in the aforementioned document DE 196 15 422, to the entirety of which reference will expressly be made. As in DE 196 15 422, the cartridge according to the invention has at least two possible ways of storing formulations or ingredients of formulations: the container of the cartridge and another chamber which is preferably formed in the closure-cap of the cartridge. Some ingredients of the formulation to be administered are stored in the chamber until ready for use, while the remaining ingredients are stored in the container, including the majority of the liquid component. This liquid component contains the solvent or suspension agent, or the majority thereof, provided for administration, preferably a solvent, and optionally other components which will be specifically described more fully hereinafter. By the term "majority thereof" is meant that part of the formulation to be applied that is not already formulated together with the active substance in the chamber. In the following text, no great distinction is drawn between solvent and mixture of solvents, i.e. the term "solvent" includes a mixture of solvents, unless otherwise stated. Conversely, however, a mixture of solvents always comprises at least two fluid, chemically-different components.

Active substances can be stored in a pharmaceutically-stable manner in the abovementioned chamber over a fairly long period of time of, for example, several months or possibly years, especially active ingredients which cannot be stored in a pharmaceutically stable manner in ethanolic solutions over the aforementioned time span.

The chamber is preferably formed in the closure-cap; however, it may be located elsewhere in the cartridge, e.g. in the interior of the container.

For reasons of clarity, in the course of this description the expression "chamber" is used for both a single chamber and also for a plurality of chambers of the same type located directly adjacent to one another, unless otherwise specified.

The chamber has at least one but preferably two openings. The closure-cap is designed so that the contents of the chambers can be transferred into the interior of the chamber through the one opening which is present in every case by means of an external influence, even when the closure-cap seals the container tightly. This opening is hereinafter referred to as the inner opening.

In addition, the chamber can optionally have a further opening. In the cartridge's closed condition, a connection between the chamber and the external environment can be made by means of this opening, so that e.g. an object, such as e.g. a plunger, a stopper, a canula, a capillary or a rod can be introduced into the chamber from outside. This opening will hereinafter be referred to as the outer opening. It is expressly emphasised that the terms "inner opening" and "outer opening" purely serve to differentiate between the terms, and no direct conclusions with regards to the position or the mutual orientation of the openings are to be made. If necessary, the inner opening can also take over the function of the outer opening.

In a preferred embodiment, the chamber is characterised in that at least one of the openings (or, in variants with only one opening, this opening) is connected to a movable plunger, sealing the opening tightly, which can be moved into or out of the chamber to open the chamber by means of an external canula or an external rod.

The inner opening of the chamber can be closed either by means of a movable stopper, a penetrable, easily-broken membrane or another movable sealing element. The outer opening optionally provided is sealed by a plunger, of such dimensions that it seals the chamber tightly on the one hand, but can be moved into the chamber by application of a force on the other hand.

In some embodiments, this plunger can have a hollow interior and have an opening. In these variants, the plunger can fill the entire chamber exactly and the active ingredient is then located inside it. If necessary, the plunger is arranged so that it simultaneously seals the outer opening and the inner opening tightly, and no further sealing elements are required to store the active ingredient, tightly sealed, within the cavity of the plunger.

When the cartridge is inserted in the inhaler, a canula or rod located in the inhaler penetrates the closure-cap and thereby directly or indirectly opens the sealing element of the inner opening. This can e.g. be achieved by the canula tearing, penetrating, opening or moving aside the sealing element, preferably starting from a point outside the chamber. If necessary, the canula can also open the sealing element from a point within the chamber. The sealing element may be a sealing foil, for example.

Alternatively, the canula may press the plunger into the chamber when the cartridge is inserted in the inhaler, so as to open the inner opening, e.g. the sealing element is either directly pierced, torn or opened by the plunger or is opened as a result of the over-pressure formed in the chamber. In doing this, the plunger is either pushed right through the chamber by the canula until it falls through the inner opening into the container, or it remains in the chamber in such a way that it does not interfere with the withdrawal of fluid through the canula.

Instead of the plunger sealing off the outer opening, one or more other equivalents can be used to perform the function of this element. These include stoppers, balls, spikes, platelets or seals of various types, e.g. sealing foils, clamp seals, plug seals or screw seals, or similar.

The apparatus according to the invention can be used as a cartridge for inhalers both for mono-preparations and also for combination preparations. In the case of mono-preparations, the active ingredient is preferably stored in a stable formulation in the chamber, the further ingredients of the pharmaceutical preparation to be applied, among them the majority of the liquid component, in the container. In the case of combined preparations, the active components can be stored as a stable formulation either in one single chamber or in various chambers. If the active ingredients which are used have significantly different shelf lives, the more sensitive active ingredient can be stored in the chamber, as described above. The other, more stable active ingredient can be stored together with the solvent or suspension agent located in the container. Naturally, a prerequisite of this is that the latter is stable in the solvent over the intended storage time of several months or years.

The shelf life of the cartridge thus filled can be substantially extended, compared with a cartridge containing the finished pharmaceutical preparation, by the delicate substances being stored in a different formulation from the one to be applied until the cartridge is inserted in the inhaler. An active substance can be stored in the chamber as a powder, granulate, in the form of a tablet, solution or as a suspension. Generally, for storage of the material or materials in the chamber, galenic formulations are preferred which promote simple and rapid dissolution of the active ingredient in the solvent when the two substances are brought together. Active substance concentrates are preferred, which constitute a further aspect of the present invention.

The active substance concentrate according to the invention contains one or more active substances which can be administered by inhalation and can preferably be used for inhalative therapy. The invention therefore also relates to the use of an active substance concentrate of this kind in inhalative therapy.

The active substance concentrate according to the invention may be converted, by dilution with a pharmacologically acceptable liquid optionally containing pharmaceutical excipients and additives, into a pharmaceutical preparation (aerosol formulation) which is converted into an inhalable aerosol with the aid of a nebuliser.

This diluent is preferably held in the container (2) when the cartridge according to the invention is used. The pharmaceutical preparation which is to be administered together with the active substance concentrate determines the precise composition of the diluent.

The active substance concentrate according to the invention refers to solutions or suspensions in which the active substance is dissolved or suspended in highly concentrated form in a pharmaceutically suitable liquid and which are characterised in that the active substance can be stored therein for a period ranging from several months to possibly several years without any deterioration in the pharmaceutical quality.

The term "active substance concentrate" denotes a solution or suspension of one or more active substances which is or are present in highly concentrated form in a pharmaceutically acceptable liquid as a solution or suspension. Suspensions are preferred, as they have proved particularly stable on storage.

The term "highly concentrated" denotes a concentration of the active substance which is usually too high to allow the corresponding solution or suspension to be used for inhalation for therapeutic purposes without being diluted. In the active substance concentrate, the concentration of the active substance (or substances) may exceed the concentration of the pharmaceutical preparation to be administered by a factor of 10 to 500, preferably 100 to 400, most preferably 250–350. According to the invention, the active substance concentration in the active substance concentrate for suspensions is between 10 mg/ml and 1000 mg/ml, preferably between 75 mg/ml and 1000 mg/ml, more preferably between 75 mg/ml and 500 mg/ml, most preferably between 100 mg/ml and 400 mg/ml, and most particularly between 250 mg/ml and 350 mg/ml. For solutions the range of concentrations is preferably between 10 mg/ml and 500 mg/ml, preferably between 75 mg/ml and 500 mg/ml, more preferably between 75 mg/ml and 200 mg/ml and most preferably between 75 mg/ml and 150 mg/ml. Thus, for example, formoterol can be present in one embodiment of the formulation according to the invention in a concentration of between 10 mg/ml and 500 mg/ml, preferably between 75 mg/ml and 500 mg/ml, more preferably between 100 mg/ml and 400 mg/ml and most preferably between 250 mg/ml and 350 mg/ml. For inhalation purposes, this formulation then has to be diluted to a concentration of about 0.9 to 1.5 mg/ml. The concentration data relate to mg of free base formoterol per ml of active substance concentrate.

The active substance(s) may be any substances which are suitable for administration by inhalation and which are soluble or capable of being suspended in the abovementioned solvent or suspension agent. The preferred active substances are, in particular, betamimetics, anticholinergics, antiallergics, leukotriene antagonists and especially steroids and active ingredient combinations thereof.

Specific Examples Include:

Tiotropium bromide, 3-[(hydroxydi-2-thienylacetyl)oxy]-8, 8-dimethyl-,8-azoniabicyclo[3.2.1]oct-6-ene-bromide

| As betamimetics: | | | |
|---|---|---|---|
| Bambuterol | Bitolterol | Carbuterol | Formoterol |
| Clenbuterol | Fenoterol | Hexoprenalin | Procaterol |
| Ibuterol | Pirbuterol | Salmeterol | Tulobuterol |
| Reproterol | Salbutamol | Sulfoneterol | Terbutalin |

1-(2-fluoro-4-hydroxyphenyl)-2-[4-(1-benzimidazolyl)-2-methyl-2-butylamino] ethanol,
erythro-5'-hydroxy-8'-(1-hydroxy-2-isopropylaminobutyl)-2H-1,4-benzoxazin-3-(4H)-one,
1-(4-amino-3-chloro-5-trifluoromethylphenyl)-2-tert.-butyl-amino)ethanol,
1-(4-ethoxycarbonylamino-3-cyano-5-fluorophenyl)-2-(tert.butylamino)ethanol.

| As anitcholinergics: |
|---|
| Ipratropium bromide |
| Oxitropium bromide |
| Tropium chloride |
| N-ᴣ-fluoroethylnortropine benzylate methobromide |

| As antiallergics: |
|---|
| Disodium cromoglycate |
| Nedocromil |
| Epinastin |

| As steroids: | |
|---|---|
| Flunisolide | Dexamethazone-21-isonicotinate |
| Seratrodast | Mycophenolate mofetile |
| Pranlukast | Zileutone |
| Butixocort | Budesonide |
| Deflazacort | Budesonide |
| Fluticasone | Promedrole |
| Mometasone furoate | Tipredane |

| -continued | |
|---|---|
| Beclometasone (or the 17, 21 dipropionate) | |
| Beclomethasone, Douglas | Icomethasone enbutate |
| Ciclometasone | Cloprednole |
| Fluocortinebutyl | Halometasone |
| Deflazacort | Aclometasone |
| Ciclometasone | Alisactide |
| Prednicarbate | Hydrocortisone butyratepropionate |
| Tixocortol pivalate | Aclometasone dipropionate |
| Lotrisone | Canesten-HC |
| Deprodone | Fluticasone propionate |
| Methylprednisolone aceponate | Halopredone acetate |
| Mometasone | Mometasone furoate |
| Hydrocortisone aceponate | Mometasone |
| Ulobetasol propionate | Aminoglutethimide |
| Triamcinolone | Hydrocortisone |
| Meprednisone | Fluorometholone |
| Dexamethazone | Betamethasone |
| Medrysone | Fluclorolone acetonide |
| Fluocinolone acetonide | Paramethasone acetate |
| Deprodone propionate | Aristocort diacetate |
| Fluocinonide | Mazipredone |
| Difluprednate | Betamethasone valerate |
| Dexamethasone isonicotinate | Beclomethasone dipropionate |
| Fluocortolone capronate | Formocortal |
| Triamcinolone hexacetonide | Cloprednol |
| Formebolone | Clobetasone |
| Endrisone | Flunisolide |
| Halcinonide | Fluazacort |
| Clobetasol | Hydrocortizone 17-butyrate |
| Diflorasone | Fluocortine |
| Amcinonide | Betamethasone dipropionate |
| Cortivazol | Betamethasone adamantoate |
| Fluodexane | Trilostan |
| Budesonide | Clobetasone |
| Demetex | Trimacinolone benetonide |

9.alpha.-chloro-6-.alpha.-fluoro-11.beta.17.alpha.-dihydroxy-16.alpha.methyl-3-oxo-1,4-androstadiene-17.beta.-methylcarboxylate-17-propionate Salbutamol, tiotropium and/or formoterol and the salts thereof, particularly formoterol, are preferably formulated in the concentrate as suspensions.

The term "pharmacologically suitable fluid" for the purposes of the present invention means a solvent or suspension agent which is not a liquefied propellant gas. Polar fluids are preferred, particularly protic fluids.

Examples of polar solvents or suspension agents for the active substance concentrate are e.g. dimethylsulphoxide or compounds which contain hydroxyl groups or other polar groups, e.g. water or alcohols—particularly ethanol, isopropylalcohol, glycols, especially propyleneglycol, polyethyleneglycol, polypropyleneglycol, glycolether, glycerol, polyoxyethylene alcohols and polyoxyethylene fatty acid esters etc.

Examples of protic liquids, which are the most preferred solvents or suspension agents in the context of the invention, are water, aqueous saline solutions with one or more pharmacologically acceptable salt(s), ethanol or a mixture thereof. In the case of aqueous ethanol mixtures, the ratio by volume of ethanol to water or to the aqueous saline solution is between 5:95 and 99:1, preferably between 40:60 and 96:4, most preferably between 75:25 and 96:4. A particularly preferred ratio is between 40:60 and 60:40.

For a saline solution as the solvent or suspension agent or as a component thereof, particularly suitable salts are those which display no or only negligibly little pharmacological activity after administration. Saline solutions are preferably used for suspension concentrates. The addition of the salt significantly reduces the dissolving power of water for the active substance or substances, so as to achieve a stabilising effect on the suspended particles. If desired, saturated saline solutions may be used. The quantity of salt depends on the precise composition of the solvent or suspension agent and its ability to dissolve the active substance. For example, formoterol should be present in dissolved form in an amount of less than 0.5% by weight, preferably less than 0.1% by weight, in an aqueous formoterol suspension in the sense of the active substance concentrate according to the invention, these amounts being based on the total amount (weight) of formoterol. However, if the amount of dissolved material is above the specified levels, it can be reduced to below these levels by the addition of salt.

As a rule, the solubility can be halved by the addition of salt, and in some cases reduced to one fifth or even less. Preferred are saline solutions with a salt content of up to 50% by weight, especially up to 20% by weight.

Both inorganic and organic salts may be used as the salts. Inorganic salts such as sodium chloride, alkali metal or ammonium halogen salts are preferred. Sodium chloride is particularly preferred. Suitable organic salts are, for example, the sodium, potassium or ammonium salts of the following acids: ascorbic acid, citric acid, malic acid, tartaric acid, maleic acid, succinic acid, fumaric acid, acetic acid, formic acid and/or propionic acid.

Cosolvents may be added to the solvent or suspension agent. Co-solvents are suitable for increasing the solubility of additives and optionally the active substance (or substances).

Preferred cosolvents are those which contain hydroxyl groups or other polar groups, for example alcohols—especially isopropyl alcohol, glycols—especially propylene glycol, polyethylene glycol, polypropylene glycol, glycol ether, glycerol, polyoxyethylene alcohols and polyoxyethylene fatty acid esters, provided that these are not already used as the solvent or suspension agent.

Other excipients and additives may also be added to the active substance concentrate according to the invention.

The term excipients and additives in this context denotes any pharmacologically suitable and therapeutically useful substance which is not an active substance but can be formulated together with the active substance (or substances) in the pharmacologically suitable solvent or suspension agent in order to improve the qualitative properties of the active substance concentrate or the pharmaceutical preparation which is to be obtained by dilution ready for inhalation. Preferably, these substances have no pharmacological activity or, in the context of the desired therapy, no appreciable or at least no undesirable pharmacological activity. The excipients and additives include, for example, surfactants for stabilising suspensions, other stabilisers, complexing agents, antioxidants and/or preservatives which prolong the duration of use of the finished pharmaceutical formulation, flavourings, vitamins, and/or other additives known in the prior art.

As surfactants the active substance concentrate may contain, for example, soya lecithin, oleic acid, sorbitan esters such as sorbitan trioleate or other surfactants known from the prior art in the usual concentrations.

It has been found that addition of an organic or inorganic acid, preferably in combination with a complexing agent, leads to improvement in the stability (shelf life) of some medicaments which contain ethanol as a solvent, especially medicaments containing steroids. This applies especially to medicament preparations which contain formoterol, flunisolide or its hydrate or hemihydrate or budenoside as active ingredient.

Examples of inorganic acids which are preferred in this respect are: hydrochloric acid, nitric acid, sulphuric acid and/or phosphoric acid. Examples of especially suitable organic acids are: ascorbic acid, citric acid, malic acid, tartaric acid, maleic acid, succinic acid, fumaric acid, acetic acid, formic acid, propionic acid and others. The preferred acids are hydrochloric acid and/or fumaric acid.

The concentration of acid is selected so that the active substance concentrate has a pH of between 2.0 and 7.0, preferably between 4.0 and 6.0 and most preferably between 4.5 and 5.5.

Examples of complexing agents which may be used on their own or in conjunction with an acid include EDTA (ethylenediaminetetraacetic acid, or a salt thereof, such as the disodium salt), citric acid, nitrilotriacetic acid and the salts thereof. The preferred complexing agent is EDTA.

Preservatives can be used to protect the concentrate from contamination with pathogenic germs. Those preservatives which are known in the prior art are suitable, especially benzalkonium chloride or benzoic acid, or benzoates such as sodium benzoate.

Suitable antioxidants are the well known pharmacologically acceptable antioxidants, especially vitamins or provitamins, as present in the human body, i.e. ascorbic acid or vitamin E.

If the active substance or substances is or are present in the active substance concentrate according to the invention as a suspension, the particles are preferably formulated in a particle size of up to 20 :m, preferably up to 10 :m and especially preferably up to 5 :m.

Preferred active substance concentrates contain only one or two active substances; active substance concentrates having one active substance are particularly preferred.

Suspensions are most preferred as the active substance concentrate.

The active substance concentrate according to the invention has the advantage that an active substance can be formulated in such a way as to remain stable over a fairly long period of time. It is not necessary for the concentrate to correspond to the composition of the finished pharmaceutical preparation, apart from the concentration of the active substance. For example, the pH of the concentrate may differ substantially from the pH of the pharmaceutical preparation which is to be administered, if this ensures a more stable solution or suspension of an active substance.

The active substance concentrate according to the invention is not usually suitable as such for direct medicinal use, particularly for inhalation. As already explained, use of the active substance concentrate comprises converting it into a pharmaceutical preparation (aerosol formulation). The term "pharmaceutical preparation" denotes a formulation of a pharmaceutical substance suitable for inhalation wherein a pharmaceutical substance or mixture of substances can be administered in the required and/or recommended concentration.

The pharmaceutical preparation is preferably such that it can be administered by inhalation using a suitable nebuliser.

A preferred method of converting the active substance concentrate into a pharmaceutical preparation suitable for administration is by diluting the active substance concentrate according to the invention with a pharmacologically suitable solvent or suspension agent.

In order to obtain the pharmaceutical preparation for administration, the active substance concentrate is diluted until the pharmaceutical preparation ready for inhalation is produced. The pharmaceutical preparation to be administered determines, together with the active substance concentrate in the chamber (17), the precise composition of the diluent in the container (2).

Examples of formulations which are suitable for administration are disclosed in WO 97/01329, to the contents of which reference is expressly made. If such formulations are to be administered within the context of the present invention, the active substance concentrate in the chamber (17) and the diluent in the container (2) should be such that when they are mixed together they produce a formulation according to or analogous to that of WO 97/01329.

In a formulation of this kind suitable for administration, the proportion of dissolved medicament in the finished pharmaceutical preparation is generally between 0.001 and 5%, preferably between 0.05 and 3%, particularly between 0.01 and 2%, these figures referring to percent by weight. In the case of solutions as the finished pharmaceutical preparation the maximum concentration of the medicament is dependent on the solubility in the solvent and the dosage required to achieve the desired therapeutic effect.

As already mentioned, aqueous or aqueous saline solutions, preferably aqueous solutions, which may contain ethanol, are preferred inter alia as solvents or suspension agents for the finished pharmaceutical preparation, i.e. the preparation suitable for inhalative or nasal application. Solutions with at least 30% (v/v) ethanol are preferred, and especially preferably with at least 50% (v/v). Especially preferred are solutions with an ethanol content of over 95% (v/v). Concentration is given in percent by volume (v/v), the remainder being water or aqueous saline solution. Ethanol which already contains small quantities of water is especially preferred—for example 96% ethanol, 4% water (v/v)—so that it is no longer hygroscopic and evaporates azeotropically.

The pharmaceutical preparation to be applied together with the active substance concentrate in the chamber (17) determine the exact composition of the diluent in the container (2).

The medicament formulation ready for use is only prepared when the cartridge is inserted in the inhaler for it is only by this action that the contents of the chamber (17) are mixed with those of the container (2). It should be pointed out here that the individual components or ingredients of the diluent are defined as specified in connection with the active substance concentrate, where these components or ingredients have been described or unless otherwise specified.

Preferred solvents or suspension agents for the dilution are propellant-free liquids, preferably polar, more particularly protic liquids.

Particularly preferred diluents are water, aqueous saline solutions with one or more pharmacologically acceptable salts, ethanol or a mixture thereof, mixtures of water and ethanol being particularly preferred. In the case of aqueous ethanol mixtures, the ratio by volume of ethanol to water or to the aqueous saline solution is such that the inhalable pharmaceutical preparation has a formulation with at least 30% (v/v) ethanol, most preferably with at least 50% (v/v). Especially preferred are pharmaceutical preparations with an ethanol content of over 95% (v/v). Concentration is given in percent by volume (v/v), the remainder being water or aqueous saline solution. Ethanol which already contains small quantities of water is especially preferred—for example 96% ethanol—so that it is no longer hygroscopic evaporates azeotropically.

It is neither obvious nor necessary for the diluent to be identical to the solvent or suspension agent of the active substance concentrate. If desired, the latter may also contain only one or a few constituents of the diluent.

It should be expressly pointed out here that the cosolvents and/or excipients or additives and/or active substances mentioned above in connection with the active substance concentrate according to the invention may also or only be dissolved or suspended in the diluent.

Preferred embodiments of the diluent contain preservatives and/or complexing agents.

Optionally, the diluent may contain a buffer substance, e.g. trisodium phosphate, disodium hydrogen phosphate, sodium dihydrogen phosphate, Na-EDTA, EDTA, mixtures thereof and other substances known from the prior art. Preferred substances are sodium dihydrogen phosphate, disodium hydrogen phosphate, trisodium hydrogen phosphate, potassium dihydrogen phosphate, potassium hydrogen phosphate, tripotassium hydrogen phosphate, and mixtures thereof. Buffer substances are particularly beneficial when the active substance concentrate suitable for storage according to the invention has a pH which differs significantly from that which is desired for the application, e.g. when this increases the stability of the active substance during storage. In this case the buffer substance is present in the diluent in a concentration such that, after mixing the active substance concentrate with the diluent, an aerosol formulation suitable for administration is obtained with the desired pH, preferably between 2.0 and 7.0, particularly between 4.0 and 6.0. most preferably between 4.5 and 5.5.

In a preferred embodiment, the pharmaceutical preparation contains a complexing agent which is preferably selected from a complexing agent mentioned in connection with the active substance concentrate. The quantity of complexing agent is up to 100 mg/100 ml, preferably up to 50 mg/100 ml. The preferred complexing agent is EDTA.

A preferred pharmaceutical preparation contains, for example, in the pharmaceutical preparation which is to be administered, 1.667% by weight of flunisolide, 0.01 mg/100 ml EDTA and ethanol (96% v/v) as solvent. It is adjusted to a pH of between 3.0 and 4.0, preferably 4.0, by the addition of acid (hydrochloric acid).

If the diluent contains one or more active substances, the diluent may contain an organic or inorganic acid, preferably combined with a complexing agent, as a stabiliser, particularly in the case of steroid-containing drugs. This applies particularly to pharmaceutical preparations which contain formoterol, flunisolide or the hydrate or hemihydrate thereof or budesonide as active substance.

As already mentioned, the pharmaceutical preparation which is to be administered together with the active substance concentrate determines the precise composition of the diluent.

Preferred pharmaceutical preparations contain one or two active substances; pharmaceutical preparations having one active substance are particularly preferred.

Neither the active substance concentrate suitable for storage according to the invention nor the pharmaceutical preparation for administration obtained by dilution contains a propellant.

Preferably, the mixing takes place at ambient temperature and under normal pressure. One advantage of the active substance concentrate according to the invention is that it can be converted by dilution into a therapeutically effective formulation and/or one which is suitable for use in a nebuliser within a very short time, e.g. within a few minutes or possibly a few seconds. The mixing can also be done by patients, who generally have no pharmaceutical knowledge.

Alternatively to the separation of the individual components of the pharmaceutical preparation to be administered, as described earlier, for the purpose of inhalation, the active substance may also be stored in the container (2), preferably as a storable solution or suspension, which does not necessarily constitute the pharmaceutical preparation to be administered. In this case, the concentration of the active substances corresponds to the concentration of the pharmaceutical preparation to be administered as described above (plus or minus 10% by weight). The chamber (17) then contains the other excipients and additives, preferably those mentioned above, for producing the pharmaceutical preparation which is to be administered. These may then take the form of powders, tablets, suspensions or solutions.

For example, an active substance may be stored as a solution or suspension in the container (2) at a pH which is more acidic or more basic than that of the pharmaceutical preparation to be administered. In this case, the chamber (17) may contain buffers, for example, preferably those described above. When the cartridge is inserted in the inhaler, the pH desired for administration is achieved by mixing the contents of the chamber (17) with the formulation in the container (2). For example, a liquid formulation containing tiotropium bromide as active substance may be stored in the container (2) at a pH of less than or equal to 3.0. The chamber (17) then contains buffer substances such as those mentioned above, e.g. the sodium and potassium di- and mono-hydrogen phosphates, in an amount which ensures that a pH of from 3.0 to 7.0, preferably from 3.0 to 4.0, is obtained when these buffers are mixed with the tiotropium formulation. These figures are merely an example of the formulation possibilities for tiotropium bromide and are not necessarily identical for other active substances mentioned. The active substance can also be stored in the container (2) as a suspension while the chamber (17) contains a pharmacologically acceptable solvent, so that a solution formulation is produced when they are mixed together.

The preferred volume of the formulations in the chamber (17) and container (2) is crucially determined by the volumes of the chamber (17) and container (2). For storage in the abovementioned cartridge, in preferred embodiments, the quantity of active substance concentrate suitable for storage according to the invention is selected to correspond to a volume of 0.001 to about 0.05 ml, preferably 0.001 to 0.02 ml.

The abovementioned examples demonstrate that the two-chamber cartridge can be used to store different components of an active substance formulation separately until the cartridge is inserted in the appropriate inhaler. It is not necessary for the components thus stored to be capable of being administered per se. All that is required is that the components thus stored are mixed together when the cartridge is inserted in the appropriate inhaler so as to produce the desired formulation ready for administration.

DESCRIPTION OF THE CARTRIDGE ACCORDING TO THE INVENTION IN DETAIL

The invention will hereinafter be described in greater detail with the assistance of concrete embodiment examples.

FIG. 2 shows an embodiment of the closure-cap (3) with an alternative sealing concept wherein, analogous to FIG. 1, only the sealing features are listed in detail. The container (2) is only indicated.

FIG. 3 shows an embodiment of the closure-cap (3) with chamber (17), a plunger (21) and a guide tube (16) in axial section.

FIG. 9 shows an embodiment of the closure-cap (3) with a plunger (21), a guide tube (16) and a chamber (17) in which two compartments are formed, in axial section.

FIG. 10 shows an embodiment of the closure-cap (3) without a precisely fitting guide track for the canula (15), in axial section.

Figure 1:
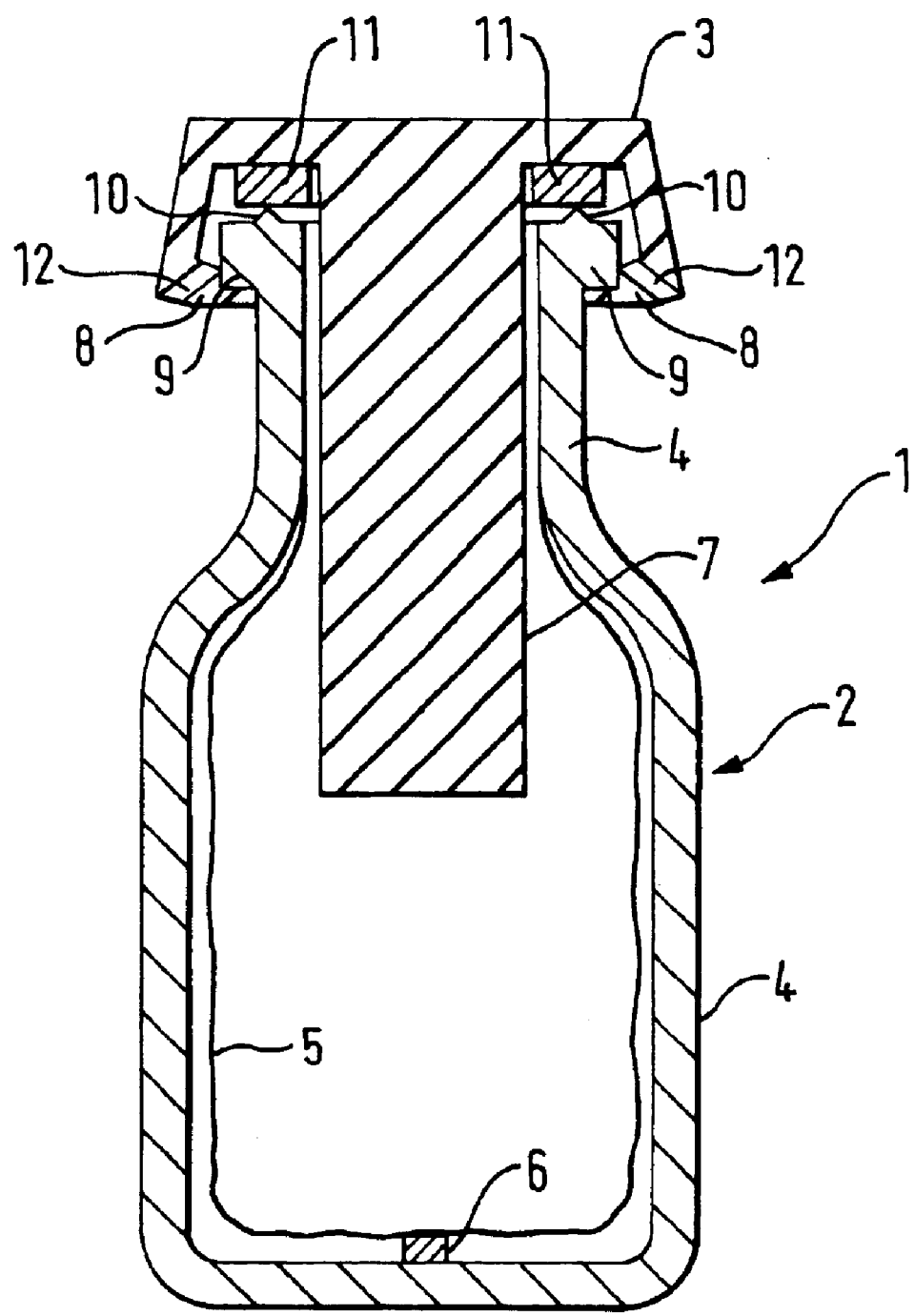
FIG. 1 shows an axial section along the longitudinal axis of the cartridge (1), according to the invention, comprising a container (2) for the solvent and a closure-cap (3) wherein substantially only the sealing features are listed. The further characteristics of the closure-cap (3) are described in more detail in the following FIGS. 3 to 11.

FIG. 1 shows an axial section along the longitudinal axis of the cartridge (1) according to the invention, comprising a container (2) for the solvent and a closure-cap (3). The drawing shows only those characteristics of the closure-cap (3) which are necessary for sealing the container (2). Further characteristics of the closure-cap (3) will be covered in greater detail in the subsequent figures.

The container (2) according to the invention comprises a "jacket" (4) and an easily-deformable inner bag (5). The inner bag (5) lines the inner wall of the jacket (4), but is not fixed to the jacket (4) except for an area in the neck of the container (2) and the web (6). The advantage of a deformable inner bag which is attached in this manner is that a fluid can be extracted therefrom via a canula without causing an under-pressure in its interior which would work against further extraction, or without the inner bag disadvantageously collapsing during removal of the fluid. In the following text, especially in the following claims, no further distinction is drawn between "container (2)", jacket (4) and "inner bag (5)", rather the term "container (2)" is exclusively used.

The closure-cap (3) has a device—here in the form of an immersed connecting piece (7)—through which some of the contents are displaced from the container (2) during the sealing process. Preferably the connecting piece (7) is such that, when the cap (3) is firmly sealing the neck of the container (2), the connecting piece (7) does not touch the neck of the container (2), or touches it only so that a gap is formed between the connecting piece (7) and the inner surface of the container (2) in the closed position of the cartridge, to allow gas or fluid to escape from inside the container (2) along the connecting piece (7) during the closing process. Alternatively, the connecting piece (7) may have one or more vertical notch(es) on its surface, along its whole length, through which gas or fluid can escape from within the container (2) during the closing process (not shown). In this case the outer diameter of the connecting piece (7) may correspond to the inner diameter of the neck of the container. In the closed position, the cap (3) seals the container (2) tightly so that no more gas or liquid can escape from inside the container (2).

A circumferential bulge (8), disposed in the interior on the lower edge of the head of the closure-cap (3), engages in the sealing position under a circumferential cylindrical ring (9) located on the outside of the container neck. In the sealed position, the intermediate space between the flat part of the closure-cap (3) and the upper edge of the container neck, which is optionally provided with a circumferential rib (10) for better sealing, is filled by a sealing ring (11) and in this way the interior of the container (2) is sealed. The interior diameter of the sealing ring (11) is chosen expediently so that it lies tightly against the connecting piece (7). The medium (gas, air or fluid) forced from the interior of the container (2) as a result of the closing process can escape via one or more ventilation openings (12) on the head of the closure-cap (3). The ventilation opening or openings (12) can also be located in other places on the cartridge, for example laterally in the cylindrical part of the cap.

FIG. 2 shows an embodiment in axial cross section where the closure-cap (3) is sealed by an aluminium sleeve (13) which is crimped. Again, only those characteristics of the closure-cap (3) which are necessary for sealing the container (2) are represented in the diagram. All other characteristics of the closure-cap (3) are described in greater detail in the following figures. The container (2) is only shown in part.

The sleeve (13) is shaped so that it has a central opening (14) for the canula (15) to pass through. The continuation of the opening (14) as a guide tube (16) for the canula (15) through the closure-cap (3) is only shown in part.

The opening (14) can be sealed by a septum as a seal of origin or in order to protect it from dust and other impurities. This method of sealing is, for example, known from injection ampoules. A seal of origin of this kind can also be formed in a closure-cap according to FIG. 1.

In the following FIGS. 3 to 11, various embodiments of the closure-cap (3) are shown in axial section. The chamber (17) is represented as an integral component of the connecting piece (7). The container (2) is not illustrated. All figures show the closure-cap with a sealing system as represented in FIG. 1. Analogous embodiments can also have a sealing system according to FIG. 2, but these are not shown.

FIG. 3 shows an embodiment of a closure-cap (3) in axial section. The central element of the closure-cap (3) is a chamber (17) which terminates at the foot of the connecting piece (7) and which contains the active ingredient(s) (22) described, which may be, for example, one or more active substances, excipients and additives which may be in the form of a concentrated solution or suspension, a powder, granules, or one of the other forms described above. Preferably, the chamber contains the active substance concentrate described above. The chamber (17) has two openings, (18) and (19). An object can be introduced into the chamber (17) from outside via the opening (18), the contents of the chamber (17) can be emptied into the container (2) via the opening (19). The opening (19) is sealed with a separating element (20) which projects beyond this and is firmly attached to the connecting piece (7). The opening (18) is sealed by a plunger (21). From the top end of the closure-cap (3), a guide tube (16) for a capillary or canula (15) for the extraction of fluid leads to the plunger (21). A septum or an O-ring seal (23) can be provided in the guide tube.

The position of the separating element (20) or the plunger (21) can vary over a wide range within the interior of the connecting piece (7), but it is preferably arranged as a function of the quantity of active ingredient (22) so that the interior space formed by the separating element (20) or by the separating element (20) and the plunger (21) contains the smallest possible volume of gas (air), preferably no gas at all.

The separating element (20) can, for example, be a foil which can be torn by pressure or which can easily be torn open by a sharp or pointed object. Heat-sealed sealing foils which are impervious to diffusion are preferred. These kind of sealing foils may contain an aluminium layer, for example. In one embodiment, the separating element (20) can have frangible points where it is attached to the side wall of the connecting piece (7) so that it tears open at these frangible points when a pressure or a force is exerted upon it. As an alternative to a sealing foil, the opening (19) can also be sealed by a stopper or a plunger (not illustrated).

The plunger (21) is made from a material which is so hard that a rounded canula cannot penetrate it, or is so inelastic that the plunger does not remain attached to the canula when the canula is pressed firmly against it. A preferred material is an elastomer, soft plastic and/or plastic such as polyethylene, silicone, EPDM (ethylene-propylene-diene-copolymer).

The shape of the plunger (21) may be cylindrical, for example. In any case, it is shaped so that it tightly seals the opening for which it is provided. The plunger (21) preferably has a length which is greater than its diameter, e.g. by a factor of between 1.2 to 2, preferably by a factor of 1.5. In this way, the plunger (21), when it is moved, is guided along its outer surface and canting is prevented. FIGS. 4a to 4g show further embodiments of the plunger (21) where one or more spikes or cutting edges (FIGS. 4a and 4b) are provided where one side is sloped (FIG. 4c) or where the plunger (21) tapers to a point (FIG. 4d). The spikes or cutting edges provided can have a very small diameter ($\mu$m to mm) and are at most long enough to reach, or almost reach, the separating element (20) in the starting position of the plunger (21), i.e. before the plunger (21) is moved through the canula (15).

Figure 4A:
FIGS. 4a to 4g show various embodiments of the plunger (21) in axial section.
Figure 4B:
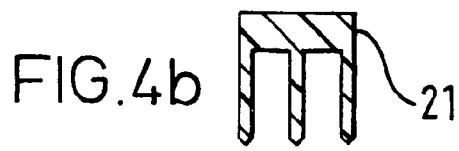
Figure 4C:
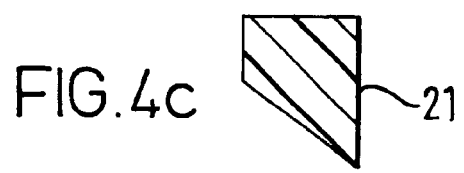
Figure 4E:
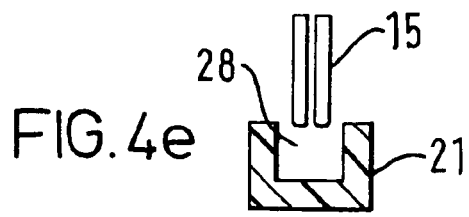
Figure 4D:
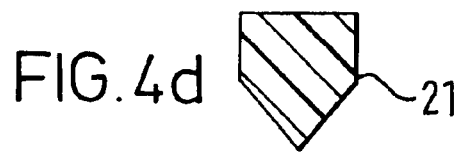

A further preferred embodiment of the plunger (21) is shown in FIG. 4e. The plunger has a recess (28) in the form of a hollow space which is open on one side. The opening in the recess (28) faces towards the head of the closure-cap (3), i.e. in the direction of the capillary or canula (15). The interior diameter of the opening or the recess (28) is greater than the exterior diameter of the canula (15). In cross section, the plunger (21) has the shape of a U with optionally angled edges. The base of the recess (28) forms the point on the plunger (21) where the canula (15) can act in order to press the plunger (21) into or through the chamber (17). The advantage of this design and arrangement is that the plunger (21) can easily taper as a result of the pressure of the canula (15) on the base of the recess (28) at the opposite end, that is, on the side of the plunger (21) which directly closes the opening (18). That is, by the application of pressure on the canula (15), the shape of the plunger (21), in cross section, changes from a U-shape to almost a V-shape. This makes it easier for the plunger (21) to pass through the opening (18). A further advantage of this shape alteration of the plunger (21) caused by pressure from the canula (15) is that the pressure of the plunger (21) on the walls which hold it is reduced so that even a tightly-fitting plunger (21) is released and can be moved by the canula (15) without canting. This embodiment is especially advantageous when the plunger (21), as e.g. shown in FIG. 3, seals the chamber (17) from within against the opening (18).

Figure 4F:
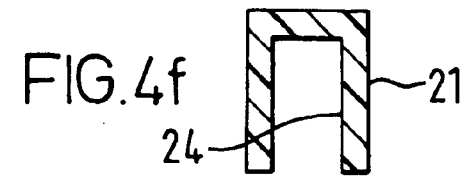
Figure 4G:
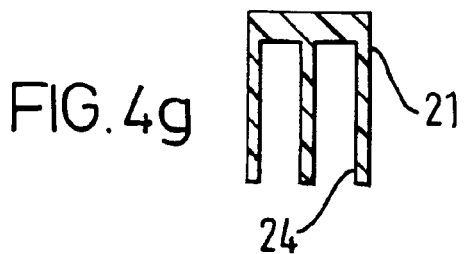

In FIG. 4f a plunger (21) with a hollow space (24) is represented which exactly, or almost exactly, fills the entire chamber (17) along its length and width. In this connection, "exactly" means that the plunger (21) has the same external dimensions as the interior of the chamber (17) or is possibly up to 5% wider than the chamber (17). The term "almost exactly" means that the plunger (21) is marginally smaller in its diameter and/or in its length than the interior of the chamber (17). It is preferred that the plunger (21) is designed as an exactly-fitting plunger. Such a variant can be advantageous on filling the closure-cap (3) but also when moving the plunger through the chamber (17) by means of the canula (15). The plunger (21) can hereby be so bedded into the chamber that the opening of the hollow space (24) is sealed by the separating element (20) (FIG. 5), or that the opening of the hollow space (24) is tightly sealed by the side wall of the chamber (17) (FIG. 6). The variant 4g shows another embodiment of a plunger (21) of the type represented in FIG. 4f in axial section, wherein the hollow space (24) is separated into two chambers by a partition for separately accommodating different ingredients in the chamber (17). Here, too, the separating element (20) seals the plunger on its open side. The opening of the plunger (21) according to FIGS. 4f and 4g can extend either over the entire width (illustrated) or only a part thereof (not illustrated).

In order to prevent canting of the plunger (21), guide means can be provided on the plunger and/or the side walls of the chamber (17), e.g. guide rails or guide ribs (not illustrated). In order to improve the sliding of the plunger (21) through the opening (18) and the chamber (17), the plunger (21) or the wall of the chamber (17) can be coated with a pharmacologically-acceptable lubricant. Such lubricants are known in the prior art and include e.g. sorbitan esters, e.g. sorbitan trioleate, oleic acid, lecithin and other fatty acids, fatty alcohols, esters of fatty acids and similar.

The guide tube (16) for canulae or capillaries can be designed so as to seal an exactly-fitting capillary (15) tightly to the connecting piece (7) when it is pushed into the connecting piece (7). If necessary, the guide tube (16) tapers as its distance from the head of the closure-cap (3) increases. Alternatively or in addition, a penetrable septum or an elastic O-ring seal (23) can be disposed at any desired position in the guide tube (16). For the sake of simplicity, the expression "septum (23)" will hereinafter be used for both a penetrable septum and an elastic O-ring seal (23). As the name implies, it is the task of the guide tube (16) to guide the canula or capillary (15) along a predefined path through the closure-cap (3) without any complications.

At the side which is open towards the head end, the guide tube (16) can have a seal of origin or a protection from impurities. These functions may also optionally be performed by the septum (23).

In a preferred embodiment, the chamber (17) has a constant interior diameter along its entire longitudinal axis. The openings (18) and (19) are located perpendicular to the longitudinal axis on the upper side or the lower side of the chamber (17). Both openings extend over the entire diameter of the chamber (17). The plunger (21) can have a marginally greater exterior diameter than the interior diameter of the chamber (17), especially when it is in its sealing position within the chamber (17) (FIG. 3). In this way, better sealing of the opening (18) is achieved. In addition, this has the advantage that the plunger (21) completely empties the chamber (17) when the former is pushed through the latter.

Figure 5:
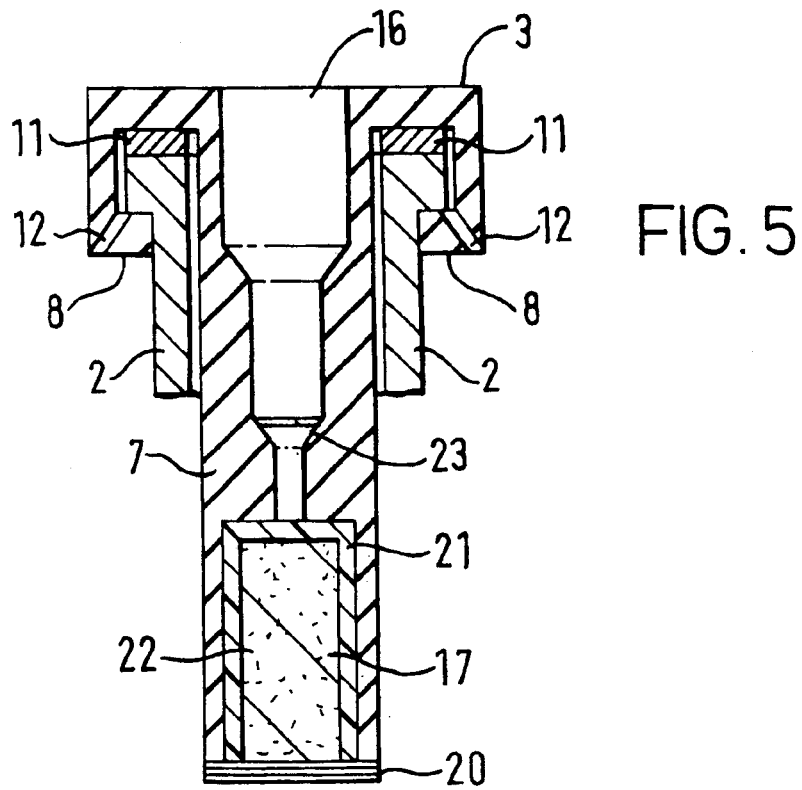
FIG. 5 shows an embodiment of the closure-cap (3) with a hollow plunger (21) for receiving the active ingredient, in axial section.
Figure 6:
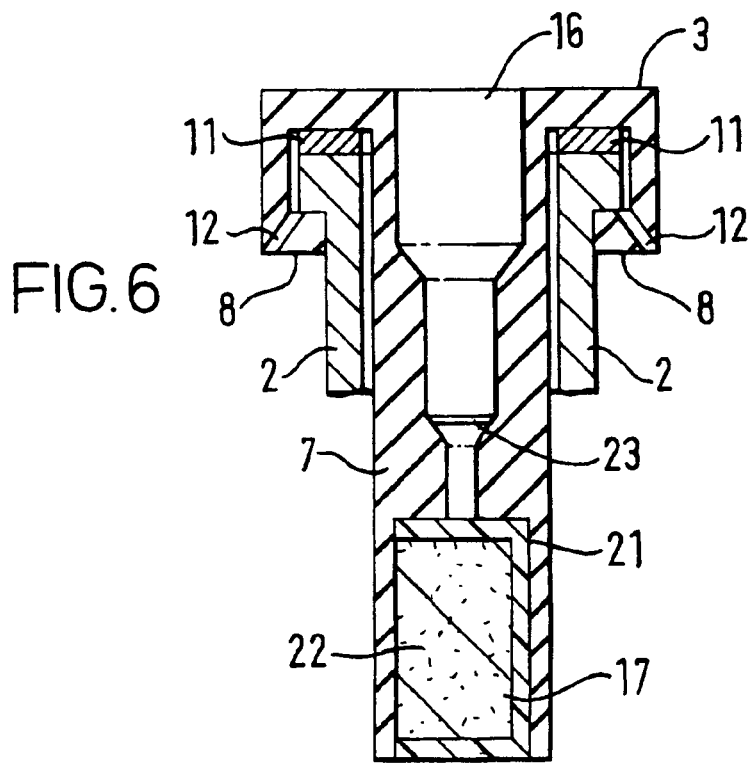
FIG. 6 shows a further embodiment of the closure-cap (3) with a hollow plunger (21), in axial section.

As already described, embodiments with a hollow plunger (21) are represented in FIGS. 5 and 6, where the active ingredient or ingredients (22) is or are stored in the hollow area (24) of the plunger instead of directly in the chamber (17). In such embodiments, the canula (15) pushes the plunger (21) right through the chamber (17) until the plunger falls into the container (2) and the contents (22) of the plunger (21) are dissolved or suspended by means of the solvent in the container (2).

Such a variant can also be designed so that the plunger cannot be pushed right through the chamber (17), but only far enough for the active ingredient (22) to be poured into the container (2) (not illustrated). In this case, guide rails and/or detents are located on the outer wall of the plunger (21) and/or the inner wall of the chamber (17), which prevent the plunger being pushed entirely through the chamber (17) (not illustrated). In this case, the side wall of the chamber (17) can also have an opening which remains sealed by the plunger (21) until the plunger (21) is moved by the canula (15). Here, the opening is designed so that the aerosol formulation ready for use can be removed through it by means of the canula (15). The plunger (21), the chamber (17), the canula (15) and the guide rails and/or detents are hereby designed so that the plunger (21) cannot block the canula (15) after it has been pushed by the canula into its end position. If desired, the canula(15) may only bring about the initial movement of the plunger (21) through the chamber (17), after which the plunger (21) falls into the detent of its end position, e.g. as a result of gravity or as a result of a further mechanism. This prevents the plunger (21) from blocking the canula (15).

Figure 7:
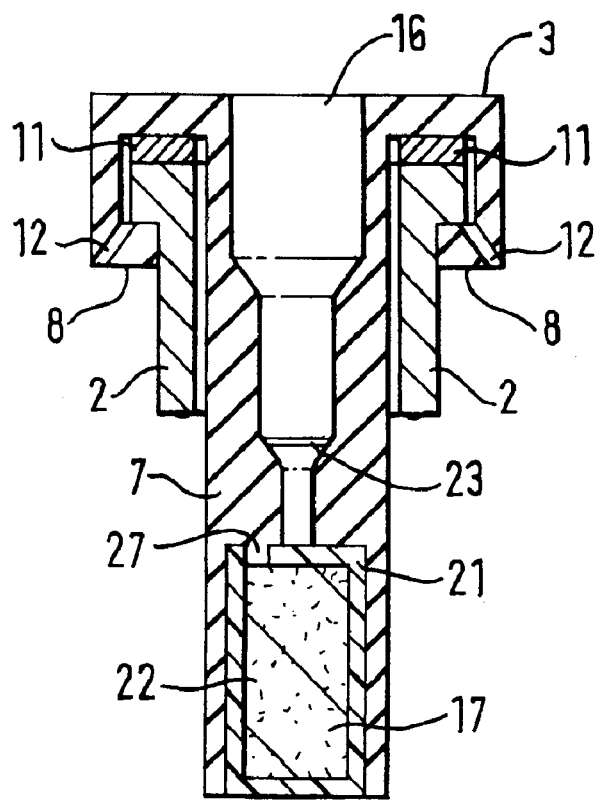
FIG. 7 shows a further embodiment of the closure-cap (3) with a hollow plunger (21), in axial section.
Figure 8:
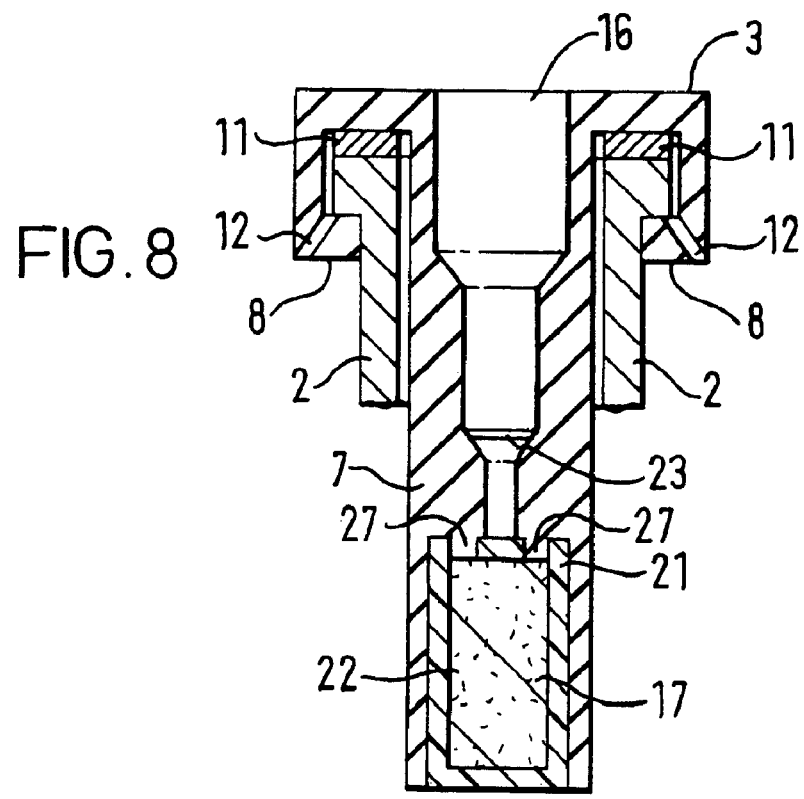
FIG. 8 shows a further embodiment of the closure-cap (3) with a hollow plunger (21), in axial section.

FIG. 7 shows a further variant with a hollow plunger (21) which entirely fills the chamber (17). The plunger (21), with its opening, is plugged onto a stopper-like projection (27), provided in the connecting piece (7), which simultaneously holds the plunger (21) in the chamber (17) and tightly seals the opening of the plunger (21). In this variant, the opening of the plunger (21) is designed so that only a part of the side wall is open. The guide tube (16) leads to a closed part of the side wall of the plunger (21) so that the canula (15) can act at this point in order to release the plunger (21) from its anchoring with the projection (27) and push it into the container (2). The plunger (21) can also have several openings which are sealed by a plurality of stopper-like projections (27) in the connecting piece (7) (FIG. 8).

In such variants, the inner opening (19) does not necessarily need to be sealed by a separating element (20), although this might be the case (not illustrated).

FIG. 9 shows an embodiment of the closure-cap (3) similar to that in FIG. 3, where the chamber (17) is divided into two compartments by means of a separating element (25). The separating element (25) is easy to open or remove, in a similar manner to the separating element (20). The compartments serve to accommodate two or more active ingredients or additives separately. In an analogous manner, more than two compartments can be provided (not illustrated).

In one embodiment, where the chamber (17) has at least two compartments, a pharmacologically-acceptable solvent with a very good dissolving power for the active ingredient can be stored in one of the compartments, e.g. the compartment which is not sealed by the separating element (20) (upper compartment). Such a solvent may be of the type defined hereinbefore, for example, or another solvent known from the prior art, e.g. pure ethanol.

In such an embodiment, the plunger (21) can be provided with one or more spikes or cutting edges. In a two-stage mechanism, the plunger (21) is firstly only pushed far enough into the chamber so that the separating element (25) is opened and the solvent flows from the upper compartment into the lower compartment and dissolves or suspends the active ingredient (22) which is located there. In a second step, the plunger (21) can then be moved further so that the separating element (20) is opened and the dissolved or suspended active ingredient flows into the container (2).

In this case, too, a penetrable membrane can be provided in place of the plunger (21). In this case, the dimension of the guide tube (16) and the upper compartment is designed so that the canula (15) can just penetrate or tear open the separating element (25), so that the solvent flows into the lower compartment and dissolves or suspends the active ingredient. The separating element (20) is then such that, or is connected with the connecting piece in such a way that the solvent destroys the connection of the separating element (20) with the connecting piece (7) to enable the solution or suspension of active ingredient to flow unimpeded into the container (2). The last-described variants are advantageous when the active ingredient in the chamber (17) is a solid which is not dissolved or suspended sufficiently rapidly in the solvent provided for the pharmaceutical formulation.

Alternatively, mixing of the solvent in the upper compartment with the contents (22) in the lower compartment can also take place directly before installation of the cartridge into the inhaler, e.g. by the user pressing the closure-cap (3) against the container (2), this implementing the first stage of the mechanism by means of a suitable apparatus. A mechanism of this type can be provided irrespective of the number of compartments in the chamber (17), i.e. if necessary only a single compartment can be provided in the chamber (17).

FIG. 10 shows an embodiment analogous to that of FIG. 3, where instead of the exactly-fitting guide tube (16) for the capillary (15), a wider guide tube (26) is provided in the closure-cap (3). In this embodiment, the plunger (21) is held on the side orientated towards the head of the closure-cap (3) by a penetrable septum or an elastic O-ring seal (23). In this case, too, the guide tube (26) can be sealed at its open end at the head of the closure-cap by a seal of origin or a protection from impurities.

In other embodiments, no guide tube (16) or no tube (26) is provided. In these cases, a septum or an elastic O-ring seal (23) is integrated into the upper side of the closure-cap (3), under which the plunger (21) or the chamber (17) is directly located. Such an embodiment is not illustrated, but is very similar to the embodiment shown in FIG. 10.

In the embodiments in FIGS. 3 to 10 described hitherto, the chamber (17), the opening (18), the opening (19) and the plunger (21) are dimensioned so that the plunger (21) tightly seals the opening (18), but can be completely pushed through the chamber (17) and the opening (19) by means of pressure on the capillary (15). In the case of the embodiments of FIGS. 3 to 6 and 9 and 10, the separating element (20) opens via the movement of the plunger (21) into the chamber (17) as a result of the force exerted through the capillary or the canula (15), in that it e.g. tears as a result of the pressure increase in the interior of the chamber (17) and/or is penetrated by one or more spikes or cutting edges provided on the plunger (21). The contents of the chamber (17) flow into the container (2) with the solvent as a result of the opening of the separating element (20). The shape and arrangement of the elements involved in this process are such that the canula (15) does not come into contact with the contents of the chamber either before or after being mixed with the contents of the container (2). In this way, blockage of the canula (15) is prevented.

Figure 11:
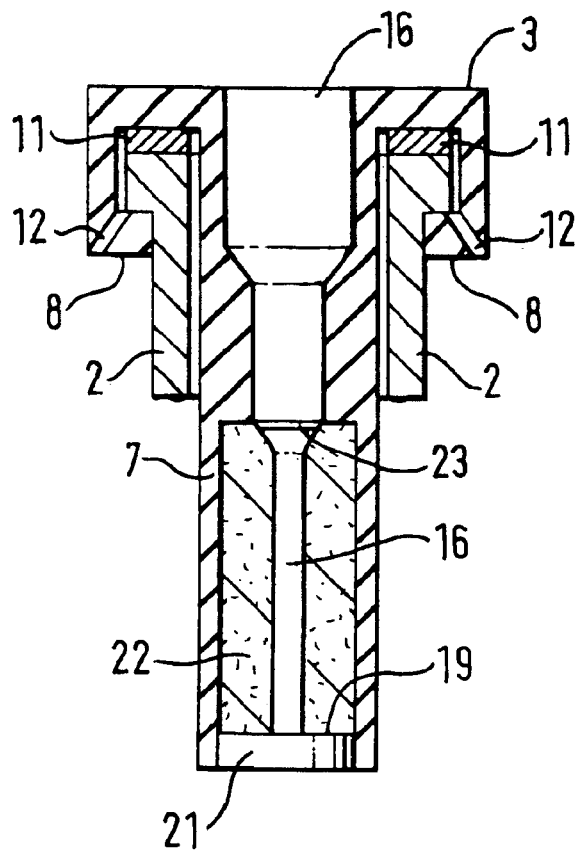
FIG. 11 shows an embodiment of the closure-cap (3) where the chamber (17) has only one opening which is sealed with a plunger (21).

Another embodiment is represented in FIG. 11 and relates to a closure-cap (3) where the interior of the connecting piece (7) is substantially hollow and thus forms the chamber (17). The guide tube (16) leads from the head of the closure-cap (3) through the chamber (17) up to the plunger (21) which is held by the lower side wall of the chamber (17) and tightly seals the chamber (17) and the guide tube (16). The plunger (21) simultaneously seals the guide tube (16) opposite the chamber (17). A septum (23) is located in the guide tube. The plunger (21) is designed so that it can be pushed into the container (2) by means of the canula or capillary (15). If necessary, the chamber (17) can be divided into various compartments by means of partitions (not represented) which are provided parallel to the longitudinal axis of the connecting piece, all of these partitions being sealed by the plunger (21) (not illustrated).

Figure 12:
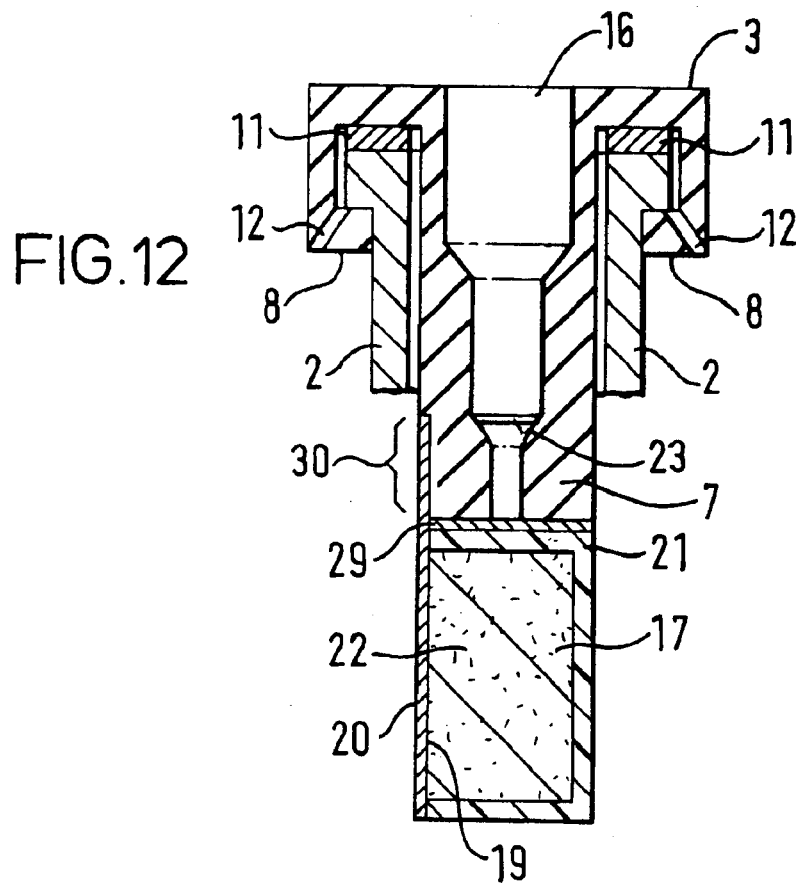
FIG. 12 shows an embodiment with a chamber (17) that can be torn off at the connecting piece (7).

FIG. 12 shows a closure-cap with a connecting piece (7) in which a guide tube (16) with a penetrable septum (23) is provided. The guide tube (16) reaches up to the foot of the connecting piece (7) where the chamber (17) is suspended via deliberately produced frangible points (29). In this embodiment, the opening (19) is parallel to the longitudinal axis of the connecting piece (7) and is tightly sealed with the separating element (20). The separating element (20) extends over the opening (19) and is fixedly connected to the connecting piece (7) at this point (30). When a capillary (15) penetrates the septum (23) and presses on the chamber (17), firstly the frangible points (29) break. The separating element (20) over the opening (19) is then torn open as a result of the inherent weight of the chamber (17) or the further pressure via the canula (15) so that the separating element (20) remains connected with the connecting piece (7); however the chamber (17) itself falls into the container (2). If necessary, the frangible points (29) can be designed as an easily-torn foil or adhesive strip, which connects the chamber (17) with the connecting piece (7) at the side opposite the separating element (20).

Alternatively, the chamber (17) can be exclusively connected with the connecting piece (7) via the separating element (20). In this case, the frangible points (29) are not provided.

If an active ingredient is to administered as a solution and is to be stored in the chamber (17) as a suspension, embodiments according to FIGS. 3, 4, 9 and 10 are preferred, especially those where the separating element (20) is designed in the form of a sealing foil with an aluminium coating. These embodiments have the advantage that an over-pressure is formed by pressure of the plunger (21) in the chamber (17), which causes the separating element (20) to tear and the suspension to flow under pressure from the chamber (17) and dissolve rapidly in the solvent in the container (2).

The container and the closure-cap are generally produced from a deformable plastic. The walls of the container are produced so that they will sufficiently give or collapse on removal of the fluid. The separating element (20) generally consists of a thin plastic foil. The separating element (20) preferably contains a thin aluminum foil.

The cartridge with medicament formulations for an inhaler, according to the invention, should have a long shelf-life. For this purpose, it is essential that the solvent cannot diffuse from the container (2) into the chamber (17) which contains the active ingredient before use. Apart from having a chamber with sufficiently thick walls, an additional aluminium coating can be applied to the outer or inner surfaces of the chamber (17).

The cartridge is preferably of such a size that it can be inserted in inhalers, such as e.g. those disclosed hereinbefore. The preferred capacity of the container (2) is approximately 5 ml, that of the chamber (17) from 0.001 to 0.5 ml, preferably from 0.001 ml to 0.2 ml, more preferably 0.001 ml to 0.05 ml, most preferably from 0.001 ml to 0.03 ml.

Suitable plastics—for example polystyrene (PS), polycarbonate (PC), polymethyl methacrylate (PMMA), acrylonitrile/butadiene/styrene copolymers (ABS), polyethylene terephthalate (PET) and other plastics are available to the skilled person for the production of such containers, and also for production of the closure-cap.

It should be emphasised that the use of the cartridge with the chamber (17) in the inhaler requires essentially the same manipulation by the patient as the use of a conventional cartridge.

EXAMPLES OF THE ACTIVE SUBSTANCE CONCENTRATE ACCORDING TO THE INVENTION

In the following text, by way of example, individual formulations are listed with concentration or quantity data. However, the examples represent only a selection from the aforementioned possible formulation combinations.

Example 1

5 mg of formoterol (particle size:5 μm) are metered as a suspension with 0.015 ml of water into the chamber (17). The pH is adjusted to 5.0 using fumaric acid. The concentration of the formoterol is 333 mg/ml.

4.5 ml of a 1:1 water/ethanol (v/v) solution are placed in the container (2). The solution contains 0.45 mg benzalkonium chloride and 2.25 mg Na-EDTA and is adjusted to a pH value of 5.0 with HCl.

After mixing, the formoterol concentration of the formulation to be administered is about 1.1 mg/ml.

Example 2

5 mg of formoterol (particle size: 5 :m) are metered as a suspension with 0.015 ml of a 20% by weight aqueous NaCl solution into the chamber (17). The pH is adjusted to 5.0 using HCl.

4.5 ml of a 1:1 water/ethanol (v/v) solution are placed in container (2). The solution contains 0.45 mg benzalkonium chloride and 2.25 mg Na-EDTA and is adjusted to a pH value of 5.0 with HCl.

Cartridges containing formoterol as active substance are prepared analogously, the content of formoterol preferably being between 100 and 400 mg/ml, most preferably between 250 and 350 mg/ml.

Example 3

In the container (2), 0.1% by weight of tiotropium bromide, 0.01% by weight of benzalkonium chloride and 0.05% by weight of EDTA are formulated in 4.5 ml of water as solvent. The pH is adjusted to 3.0 using hydrochloric acid. The chamber (17) contains a 10 mg tablet consisting of 0.5 mg of the buffer substance $Na_2HPO_4 \times 2\, H_2O$ and 9.5 mg of NaCl. When the cartridge is inserted in the inhaler, the buffer substance from the chamber (17) is mixed with the solution in the container (2) and a pH of 3.5 is thus achieved.

Analogously, cartridges are prepared with tiotropium bromide as active substance, wherein the content of tiotropium bromide is preferably between 0.002 and 0.4% by weight, most preferably between 0.0005 and 0.2 by weight. The pH of the solution in the container (2), before mixing with the buffer in the chamber (17), is preferably below 4.0 in these cases, most preferably between 2.0 and 3.0 and particularly between 2.5 and 3.0.

What is claimed is:

1. An apparatus comprising: a closure-cap and a container in the form of a cartridge for separate storage of an active ingredient and a pharmacologically acceptable liquid, wherein the closure-cap has: (i) a guide tube for passage of a capillary or canula through the closure-cap, (ii) a connecting piece which at least partially enters the container through an upper edge of the container's neck when the closure-cap is pushed onto the neck, (iii) a chamber integral within the connecting piece and including at least one opening, and (iv) a plunger disposed downward from the upper edge of the neck within the chamber and sealing the at least one opening thereof, the plunger including at least three sides defining a hollow space to hold one of the active ingredient and the pharmacologically acceptable liquid, and at least one aperture that is sealed when the plunger is in a first position and that opens when the plunger is in a second position.

2. An apparatus according to claim 1, wherein a penetrable septum is located in the closure-cap between the plunger and an upper extremity of the closure cap.

3. An apparatus according to claim 1, wherein a penetrable septum or an elastic O-ring seal is formed in the guide tube.

4. An apparatus according to claim 1, wherein the chamber has a further opening which is sealed by a penetrable, tearable or movable separating element.

5. An apparatus according to claim 4, wherein the separating element is formed as a sealing foil that also seals the at least one aperture of the plunger when it is in the first position.

6. An apparatus according to claim 1, wherein the chamber has two or more compartments which are arranged one above the other and are each sealed from the other by a penetrable, tearable or movable separating element.

7. An apparatus according to claim 1, wherein the plunger has the shape of a cylinder with a ratio of length to diameter of 1.2 to 2.0.

8. An apparatus according to claim 1, wherein the at least one aperture opens on one side of the plunger facing a wall of the chamber.

9. An apparatus according to claim 8, wherein the wall seals the hollow space when the plunger is in the first position.

10. An apparatus according to claim 8, wherein the hollow space is sealed by a separating element.

11. An apparatus according to claim 1, wherein the hollow space is divided by at least one partition wall into two or more compartments which are sealed from one another, and each compartment is sealed by a separating element or by a wall of the chamber.

12. An apparatus according to claim 1, wherein a recess is formed in the plunger opening toward a head of the closure-cap.

13. An apparatus according to claim 1, wherein the plunger or at least one wall of the chamber is coated with a pharmacologically acceptable lubricant.

14. An apparatus according to claim 13, wherein the pharmacologically acceptable lubricant is selected from the group consisting of oleic acid, lecithin and a sorbitan ester.

15. An apparatus according to claim 1, wherein the at least one aperture of the plunger opens toward the neck of the container.

16. An apparatus according to claim 15, wherein the at least one aperture of the plunger leading to the hollow space is sealed by one or more projections formed on the connecting piece when the plunger is in the first position.

17. An apparatus according to claim 1, wherein the at least one aperture of the plunger leading to the hollow space is sealed by one or more projections formed on the connecting piece when the plunger is in the first position.

18. An apparatus according to claim 1, wherein the plunger is up to 5% wider than the opening which it closes.

19. An apparatus according to claim 1, wherein the chamber contains a pharmaceutical concentrate in the form of a suspension or a solution in a pharmacologically acceptable propellant-free liquid with one or more active substances, the active substance or substances being suitable in particular for inhalative therapy.

20. An apparatus according to claim 19, wherein the pharmacologically acceptable propellant-free liquid is water, an aqueous solution with pharmacologically acceptable salt, ethanol or a mixture thereof.

21. An apparatus according to claim 19, wherein the active substance is selected from the group of betamimetics, anticholinergics, antiallergics, leukotriene antagonists, steroids and a mixture thereof.

22. An apparatus according to claim 21, wherein the active substance is selected from formoterol, tiotropium, salbutamol, a salt thereof and a mixture thereof.

23. An apparatus according to claim 22, wherein the chamber contains a suspension of formoterol in a concentration of between about 75 mg/ml and about 500 mg/ml.

24. An apparatus according to claim 19, wherein the concentration of the active substances is between about 75 mg/ml and about 1000 mg/ml.

25. An apparatus according to claim 24, wherein the concentration of the active substance is between about 75 mg/ml and about 500 mg/ml.

26. An apparatus according to claim 25, wherein the concentration of the active substance is between about 100 mg/ml and about 400 mg/ml.

27. An apparatus according to claim 19, wherein the container contains a solution of tiotropium bromide in an amount of between about 0.0002 and about 0.4% by weight, and having a pH of from about 2.0 to about 4.0.

28. An apparatus according to claim 27, wherein the container contains a solution of tiotropium bromide in an amount of between about 0.0005 and about 0.2% by weight.

29. An apparatus according to claim 27, wherein the container contains a solution of tiotropium bormide in an amount of about 0.1% by weight.

30. An apparatus according to claim 1, wherein the active substance concentrate in the chamber contains an acid, a preservative, a complexing agent, or a mixture of such elements.

31. An apparatus according to claim 1, wherein the container contains a pharmacologically acceptable propellant-free liquid, which optionally contains an acid, a complexing agent, a preservative, a surfactant, a buffer or a mixture of such elements.

32. An apparatus according to claim 31, wherein the solvent or suspension agent contains one or more medicaments selected from the group of betamimetics, anticholinergics, antiallergies, leukotriene antagonists, steroids and a mixture thereof.

33. An apparatus according to claim 31, wherein the chamber contains a buffer substance.

34. An apparatus according claim 1, wherein the cartridge is operable for use with an atomizer.

35. An apparatus comprising:
a container having a neck leading to a volume for storing one of an active ingredient and a pharmacologically acceptable liquid;
a closure cap including: (i) a connecting piece which at least partially enters the volume through the neck when the closure-cap engages the container, (ii) a chamber integral within the connecting piece and including at least one opening at a lower end thereof, and (iii) a guide tube extending through the closure cap to an upper end of the chamber;
a plunger disposed downward from the neck and sealing an upper end of the chamber when in a first position, the plunger being movable by inserting a device through the guide tube; and
a separating element sealing the opening at the lower end of the chamber,
wherein movement of the plunger from the first position to a second position toward the lower end of the chamber breaks the seal by the separating element and permits the other of the active ingredient and the pharmacologically acceptable liquid to exit the chamber and enter the volume of the container.

36. An apparatus according to claim 35, wherein the plunger, chamber and separating element are adapted such that movement of the plunger toward the second position increases pressure within the chamber that causes the seal formed by the separating element to break.

37. An apparatus according to claim 36, wherein the separating element is formed from at least one of a sealing foil and a stopper.

38. An apparatus according to claim 36, wherein the separating element includes one or more frangible points that assist in breaking the seal under pressure.

39. An apparatus according to claim 36, wherein a side of the plunger facing the separating element at least one of slops, tapers to a point, has one or more spikes, and has one or more or cutting edges that assist in breaking the seal.

40. An apparatus according to claim 35, to wherein the plunger, chamber and separating element are adapted such that the plunger engages the separating element as the plunger moves toward the second position that causes the seal formed by the separating element to break.

41. An apparatus according to claim 40, wherein the separating element includes one or more frangible points that assist in breaking the seal under pressure.

42. An apparatus according to claim 40, wherein the separating element is formed from a sealing foil.

43. An apparatus according to claim 42, wherein a side of the plunger facing the separating element at least one of slops, tapers to a point, has one or more spikes, and has one or more or cutting edges that assist in breaking the seal.

44. An apparatus comprising:
a container having a neck leading to a volume for storing one of an active ingredient and a pharmacologically acceptable liquid;
a closure cap including: (i) a connecting piece which at least partially enters the volume through the neck when the closure-cap engages the container, (ii) a chamber integral within the connecting piece and including at least one opening at a lower end thereof, and (iii) a guide tube extending through the closure cap to an upper end of the chamber; and
a flexible plunger disposed downward from the neck and sealing an upper end of the chamber when in a first position, the plunger having a first surface communicating with the guide tube such that a cannula may engage the first surface through the guide tube,
wherein the plunger is operable to deform in response to force applied by the cannula such that frictional forces between the plunger and walls of the chamber are reduced.

45. The apparatus of claim 44, wherein the deformation of the plunger in response to the force applied by the cannula reduces canting within the chamber.

46. The apparatus of claim 44, wherein:

the plunger includes a substantially planar second surface oppositely facing from the first surface; and the deformation of the plunger in response to the force applied by the cannula causes the second surface to become non-planar.

47. The apparatus of claim 46, wherein the second surface becomes substantially tapered in cross-section in response to the deformation of the plunger.

48. The apparatus of claim 47, wherein the second surface becomes substantially V-shaped in cross-section in response to the deformation of the plunger.

49. The apparatus of claim 46, wherein the plunger includes a cup-shaped portion having an opening and an interior volume, the first surface being disposed away from the opening within the interior volume.

50. The apparatus of claim 49, wherein the opening and the first surface include dimensions transverse to the direction of the guide tube that are greater than a diameter of the cannula.

51. The apparatus of claim 49, wherein the interior volume and the first surface are substantially centrally located within the plunger.

52. The apparatus of claim 44, wherein movement of the plunger from the first position to a second position toward the lower end of the chamber permits the other of the active ingredient and the pharmacologically acceptable liquid to exit the chamber and enter the volume of the container.

* * * * *